United States Patent [19]

Manwaring et al.

[11] Patent Number: 5,711,299
[45] Date of Patent: Jan. 27, 1998

[54] SURGICAL GUIDANCE METHOD AND SYSTEM FOR APPROACHING A TARGET WITHIN A BODY

[76] Inventors: Kim H. Manwaring, 3440 E. Tonto Dr., Ahwatukee, Ariz. 85044; Mark L. Manwaring, SW 1430 Wadleigh Dr., Pullman, Wash. 99163

[21] Appl. No.: 592,053

[22] Filed: Jan. 26, 1996

[51] Int. Cl.⁶ ............................................. A61B 5/05
[52] U.S. Cl. ..................... 128/653.1; 128/899; 600/117
[58] Field of Search ................... 128/653.1, 899; 324/200, 207.11, 207.22; 600/117

[56] References Cited

U.S. PATENT DOCUMENTS 5,558,091  9/1996  Acker et al. ............................ 128/899
5,592,939  1/1997  Martinelli ............................ 128/653.1

*Primary Examiner*—Jennifer Bahr
*Assistant Examiner*—Eric F. Winakur
*Attorney, Agent, or Firm*—Meschkow & Gresham, P.L.C.

[57] ABSTRACT

A surgical guidance system includes a magnetic field generator carried by a support frame, a guidance system controller, at least one magnetic field sensor located at a surgical instrument, and a feedback display device. The guidance system indicates the position of the surgical instrument relative to a trajectory as the surgical instrument approaches a surgical target within a body. The magnetic field generator establishes a magnetic field having geometric characteristics that indicate the trajectory from an initial point to the target. The sensors detect the distinguishable orientation of the magnetic field along the trajectory, and the feedback display device indicates whether the surgical instrument is aligned or misaligned with the trajectory. The magnetic field generator is adjustable upon the support frame such that the approach angle and position of the trajectory may be selected.

25 Claims, 5 Drawing Sheets

SURGICAL GUIDANCE METHOD AND SYSTEM FOR APPROACHING A TARGET WITHIN A BODY

TECHNICAL FIELD OF THE INVENTION

The present invention relates generally to medical equipment. More specifically, the present invention relates to a system for guiding a surgical instrument to a target within a body.

BACKGROUND OF THE INVENTION

A number of frame and frameless stereotactic systems have been developed to assist surgeons during various procedures that require an instrument to travel to a target within a body. Typically, a surgeon analyzes images of the body (e.g., CT scans, MRI scans, or PET scans) to determine the location of the target and to determine a desirable trajectory along which the instrument should travel during the surgical procedure. Frameless stereotactic systems do not require the body to be mechanically fixed to a reference frame or other device during the surgical procedure. In addition, frameless stereotactic systems are generally less invasive and allow a surgeon to move a surgical instrument in any desired direction without being restricted by cumbersome mechanical structures. As such, frameless stereotactic systems often reduce the amount of patient trauma associated with certain surgical procedures while providing the surgeon with an adequate amount of positional freedom during surgery.

Conventionally, stereotactic systems attempt to determine the precise location of the surgical instrument relative to a reference point within a coordinate system. Some frameless stereotactic systems utilize sophisticated optical, RF, magnetic, audio, or other methodologies to generate a three dimensional reference volume around the surgical area. Typically, the surgical instrument carries a system-compatible emitter or sensor, and the position of the instrument is determined relative to a number of reference points to facilitate precise location analysis anywhere within the reference volume.

Many surgical procedures require the surgeon to approach a target along a predetermined trajectory. As such, knowledge of the precise location of the surgical instrument within the entire field of operation may be useless to the surgeon. In other words, the surgeon may primarily need guidance to the predetermined target rather than knowledge of the exact location of the instrument at all times.

Frameless stereotactic systems that determine the position of the surgical instrument may employ a number of sensitive electronic components. Due to the precision and sensitivity of the electronic components, such systems may be unreliable. In addition, medical technicians may be required to perform complex calibration procedures and/or periodic maintenance for a typical frameless stereotactic system. Furthermore, a single system may require a number of compatible surgical instruments to facilitate flexible use in a variety of different surgical procedures. This approach provides complex and expensive systems that do not get widespread use due to the complexity and expense.

The sterilization of surgical equipment is an additional procedure that may affect the economic practicality of some frameless stereotactic systems. Known stereotactic systems typically utilize system-specific surgical instruments that incorporate some type of location sensor or emitter. These surgical instruments must be sterilized carefully to ensure that the sensitive detection equipment is not damaged. Due to the high cost of such equipment, surgeons must sterilize and reuse the surgical instrument rather than dispose of the sensor or emitter components after each use.

Conventional positioning systems may be difficult to use, due in part to the complex nature of the systems. For example, systems that precisely locate and orient the instrument may overly restrict the amount of positional freedom available to the surgeon. Such stereotactic systems may erroneously indicate the position of the surgical instrument if the surgeon axially rotates the instrument within his or her hand. Such rotational freedom may be desirable during free-hand surgery. In addition, the data generated by a conventional system may be difficult to interpret unless the operator is very familiar with the particular system. Thus, surgeons and medical technicians may require extensive training before they can efficiently operate conventional systems.

SUMMARY OF THE INVENTION

Accordingly, it is an advantage of the present invention that an improved surgical guidance method and system for approaching a target within a body are provided.

A further advantage is that the surgical guidance system does not restrict axial rotation of a surgical instrument as a surgeon directs the instrument along a trajectory toward the target.

Another advantage is that a surgical guidance system according to the present invention may be implemented using relatively inexpensive components.

Another advantage is that the guidance system need not quantitatively identify the position of the surgical instrument during the surgical procedure.

A further advantage is that sterilization costs may be reduced by disposing of an instrument-mounted sensor component after the surgical procedure is performed.

The above and other advantages of the present invention are carried out in one form by a system for guiding a surgical instrument to a target within a body. The system produces a magnetic field having geometric characteristics that indicate a trajectory from an initial point to the target. A magnetic field sensor located at the surgical instrument detects the orientation of the magnetic field, and a feedback device indicates the position of the surgical instrument relative to the trajectory.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

DETAILED DESCRIPTION OF THE PREFERRED EMBODIMENTS

Figure 1:
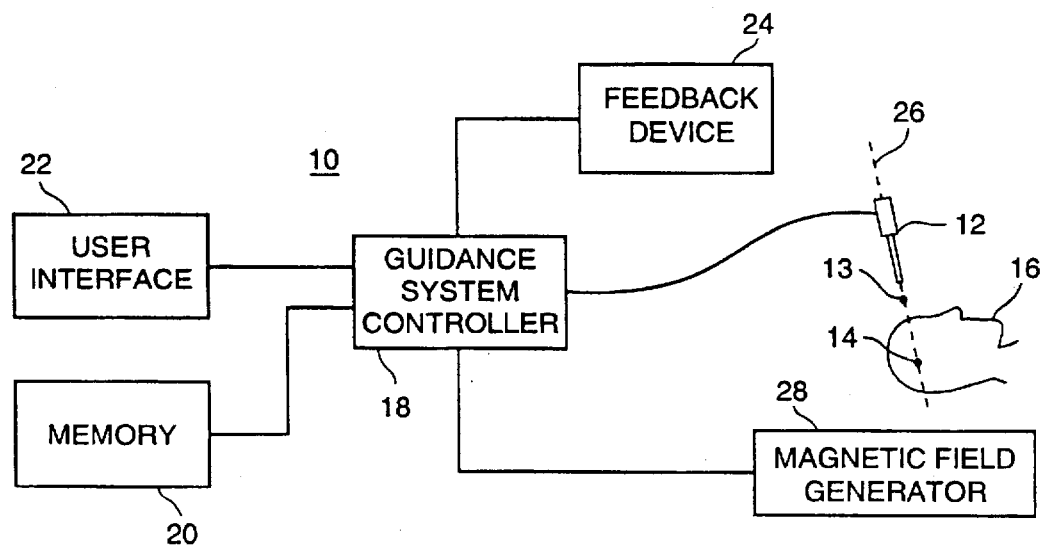
FIG. 1 is a block diagram depiction of a surgical guidance system.

FIG. 1 illustrates a surgical guidance system 10. System 10 provides information that aids the guidance of a surgical instrument 12 to a target 14 located within a body 16. Surgical instrument 12 represents any instrument which may be inserted into body 16. While the present invention may employ any type of surgical instrument 12, an endoscope represents one particularly desirable form of surgical instrument 12. FIG. 1 illustrates body 16 in the form of a human head because system 10 is particularly suited to endoscopic surgery within the brain. However, system 10 is not limited to brain or endoscopic surgeries. System 10 may be used in any surgery that involves guiding a surgical tool along a selected trajectory to target 14.

System 10 includes a guidance system controller 18. Conventional medical, personal, or industrial computer components, such as a processor board, may serve as controller 18. At a minimum, controller 18 couples to a memory 20, a user interface 22, and a feedback device 24. Memory 20, user interface 22, and feedback device 24 may be configured as conventional computer components commonly used in connection with medical, personal, industrial, and other computers.

Memory 20 stores data used by system 10 and computer programs which define the operation of system 10. For example, system 10 may be configured to display tomograms formed in accordance with conventional CT, MRI, PET, or other tomographic techniques. Digitized tomograms and other data may be stored in memory 20 until processed by system 10.

User interface 22 allows a surgeon or other user of system 10 to enter selections and otherwise provide data to system 10. Such selections control the operation of system 10 before, during, and after surgery. Conventional touch screens, remote control devices, keyboards, pointing devices, and the like all represent suitable examples of user interface 22. User interface 22 is desirably located for easy manipulation by the surgeon during surgery and sterilized at least to the extent that it is manipulated by the surgeon during surgery.

Feedback device 24 is configured to indicate the position of surgical instrument 12 relative to a trajectory 26. Feedback device 24 is desirably a CRT, LCD, plasma, or other video terminal or projection device which visually presents information to the user of system 10. However, nothing prevents feedback device 24 from indicating the relative position of surgical instrument 12 via audio, mechanical, or other signaling methodologies. Regardless of where other components of system 10 may be located, feedback device 24 is desirably located so that its visually presented information may be conveniently viewed by the surgeon during surgery. Certain visual characteristics of feedback device 24 are described below in connection with FIG. 11.

Controller 18 additionally couples to a magnetic field generator 28. Magnetic field generator 28 is configured to produce a magnetic field 30 (see FIGS. 2, 4 and 5) having geometric characteristics that indicate trajectory 26. Although not shown, an alternate implementation is configured with magnetic field generator 28 coupled to surgical instrument 12. For purposes of this description, trajectory 26 may be defined as the path extending between an initial point 13 and target 14. Surgical instrument 12 should follow trajectory 26 during the surgical procedure. Prior to surgery, the surgeon determines trajectory 26 according to various factors such as the location of target 14, the type of surgical procedure to be performed, critical or eloquent areas that must be avoided, and the surgical position of body 16. The initial point 13 may be an entry point upon body 16, a point outside body 16, or any suitable reference location chosen by the surgeon. During surgery, the surgeon causes surgical instrument 12 to follow trajectory 26 with the assistance of system 10.

Figure 2:
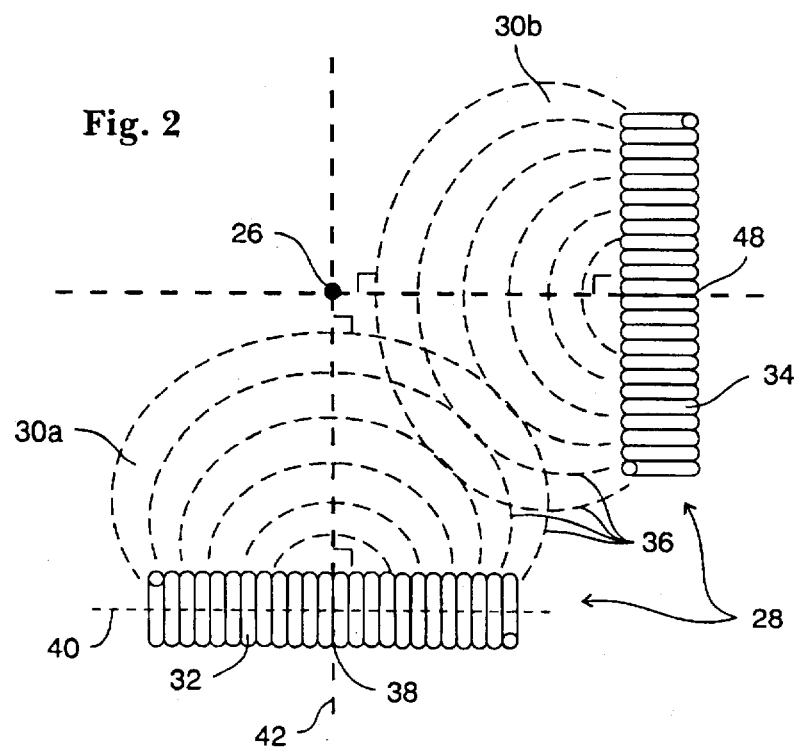
FIG. 2 is a schematic representation of magnetic fields generated by two electromagnets.
Figure 3:
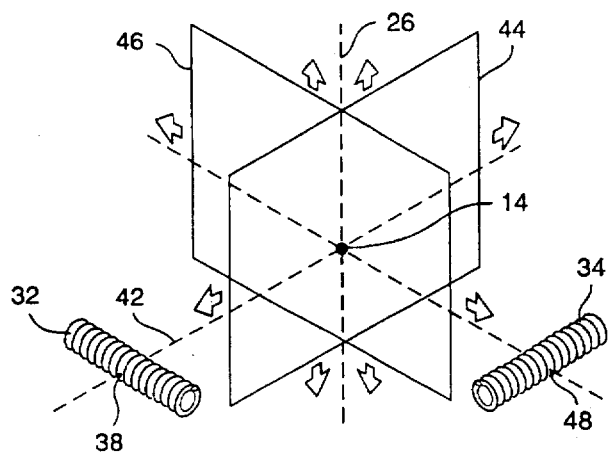
FIG. 3 is a schematic representation of a trajectory as indicated by the geometric characteristics of the magnetic fields.

System 10 senses the geometric orientation of magnetic field 30 emitted from magnetic field generator 28. With reference to FIGS. 2–3, the relationship between magnetic field 30, magnetic field generator 28, and trajectory 26 is illustrated. FIG. 2 represents a cross sectional view through magnetic field 30 looking directly down trajectory 26 (depicted as a point in this view). It should be understood that FIG. 2 merely describes certain characteristics of magnetic field 30. In practice, the configuration of magnetic field 30 and magnetic field generator 28 may be altered according to specific system requirements.

According to the preferred embodiment, magnetic field generator 28 includes at least a first generator element and a second generator element configured as a first electromagnet 32 and a second electromagnet 34, respectively. In one embodiment, first and second electromagnets 32 and 34 are formed from a wire coil wound around a cylindrical iron or steel core in a tight helix. FIG. 2 illustrates a portion of a magnetic field 30a generated by first electromagnet 32 and a portion of a magnetic field 30b generated by second electromagnet 34.

Magnetic field 30 is produced by the periodic generation of magnetic fields 30a and 30b. First and second electromagnets 32 and 34 are alternatively driven such that magnetic fields 30a and 30b do not interfere with one another. According to one aspect of the preferred embodiment, the driving source alternates between first and second electromagnets 32 and 34 at a frequency of approximately 15–25 Hz. Of course, the oscillation frequency may be varied according to the desired detection sensitivity of system 10.

Although magnetic field 30 is a continuous and three dimensional field, it is represented in the Figures by two dimensional discrete magnetic flux lines 36 for the sake of simplicity. In addition, the following description of magnetic field 30a generated by first electromagnet 32 also applies to magnetic field 30b generated by second electromagnet 34.

Magnetic field 30a is generated such that the influence of static magnetic fields and magnetic materials present in the environment are reduced. According to a preferred technique, first electromagnet 32 is driven by an alternating current source having a frequency of approximately 100–150 Hz. The periodic reversal of magnetic field 30a substantially cancels any adverse effects that may otherwise be caused by any static magnetic fields.

According to one aspect of the preferred embodiment, magnetic field 30a generated by first electromagnet 32 may define a first magnetic center 38 located centrally along a longitudinal axis 40 associated with first electromagnet 32. For illustrative purposes, FIG. 2 shows a center line 42 that perpendicularly intersects longitudinal axis 40 at first magnetic center 38. Magnetic flux lines 36 intersect center line 42 at substantially a right angle. Thus, in three dimensional space, a first plane 44 (see FIG. 3) that perpendicularly bisects first electromagnet 32 through first magnetic center 38 is defined by the orientation of magnetic field 30a.

A second plane 46 is similarly defined by the orientation of magnetic field 30b generated by second electromagnet 34. In like manner as first plane 44, second plane 46 perpendicularly bisects second electromagnet 34 through a second magnetic center 48. FIG. 3 shows a graphical representation of first and second planes 44 and 46. First and second planes 44 and 46 are utilized herein to illustrate the geometric characteristics of magnetic field 30, and are not intended to convey structural elements of system 10. In addition, planes 44 and 46 may extend indefinitely into three dimensional space. For clarity, magnetic field 30 is not shown in FIG. 3. Trajectory 26 is indicated by the intersection of first and second planes 44 and 46.

First and second electromagnets 32 and 34 are preferably physically adjustable in their respective longitudinal directions such that their respective magnetic centers 38 and 48 align with target 14. In addition, first and second electromagnets 32 and 34 may be pivotable about their respective magnetic centers 38 and 48, or other suitable reference axes, such that trajectory 26 follows a desired approach angle relative to a reference line (described below).

Figure 4:
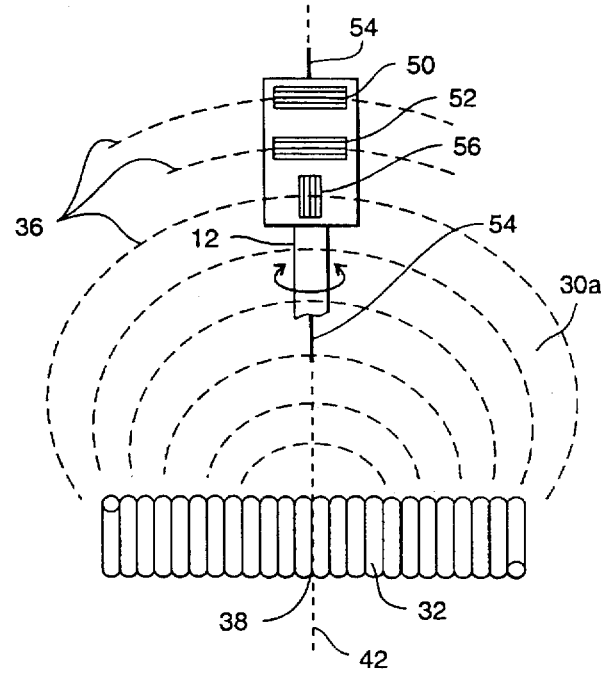
FIG. 4 shows the location of magnetic field sensors relative to a surgical instrument within a magnetic field generated by an electromagnet.

FIG. 4 shows the location of a first magnetic field sensor 50 and a second magnetic field sensor 52 relative to surgical instrument 12. First and second sensors 50 and 52 are preferably aligned with an instrument axis 54 of surgical instrument 12. Instrument axis 54 is preferably the longitudinal axis of surgical instrument 12. First sensor 50 is desirably spaced apart from second sensor 52 along instrument axis 54. The spacing between first and second sensors 50 and 52 may be selected according to the desired detection sensitivity of system 10.

The orientation of magnetic field 30 is preferably detected by first and second sensors 50 and 52. Feedback device 24 is in communication with first and second sensors 50 and 52 via controller 18 (see FIG. 1). First and second sensors 50 and 52 may be integral to surgical instrument 12 or part of a separate housing (not shown) that removably couples to surgical instrument 12. The removable sensor housing allows first and second sensors 50 and 52 to be adapted to existing instruments as necessary. In addition, the removable sensor housing may be disposable, which may be desirable to reduce equipment sterilization costs.

First and second sensors 50 and 52 are each adapted to detect the orientation of magnetic field 30. First and second sensors 50 and 52 are preferably configured to detect components of magnetic field 30 that are parallel to instrument axis 54. In the preferred embodiment, first and second sensors 50 and 52 are conventional magnetometers positioned such that their sense windings are wound in a perpendicular direction relative to instrument axis 54. Magnetometers are well known to those skilled in the field of magnetics and will not be described in detail herein.

FIG. 4 schematically depicts magnetic field 30a emitted by first electromagnet 32. First and second sensors 50 and 52 are configured such that substantially zero magnitude is detected in magnetic field 30a where magnetic flux lines 36 are at substantially right angles to instrument axis 54. Due to the geometric characteristics of magnetic field 30a (described above) and the locations of first and second sensors 50 and 52 relative to instrument axis 54, first and second sensors 50 and 52 will simultaneously detect a null (zero magnitude) in magnetic field 30a when they both are substantially collinear with first magnetic center 38.

First and second sensors 50 and 52 function in a similar manner when detecting magnetic field 30b emitted by second electromagnet 34 (see FIGS. 2-3). When first and second electromagnets 32 and 34 are alternatively driven to produce magnetic field 30, first and second sensors 50 and 52 detect a relative null in magnetic field 30 when instrument axis 54 is aligned with trajectory 26. The perpendicular orientation of magnetic field 30 along trajectory 26 preferably exists throughout trajectory 26. In addition, the characteristic orientation of magnetic field 30 is preferably constant throughout trajectory 26. In other words, first and second sensors 50 and 52 detect the null in magnetic field 30 anywhere along trajectory 26.

Due to the operation of first and second sensors 50 and 52, surgical instrument 12 may be rotated within the surgeon's hand without adversely affecting the performance of system 10. For example, system 10 may be capable of accurately indicating the displacement of surgical instrument 12 relative to trajectory 26 notwithstanding the rotational position of surgical instrument 12. The rotational degree of freedom of surgical instrument 12 is depicted by the arrow in FIG. 4. The null-detection capabilities of first and second sensors 50 and 52 are not affected by rotation of surgical instrument 12 about instrument axis 54.

System 10 may also be configured to determine distance between a reference point (not shown) on surgical instrument 12 and target 14. For example, system 10 may include a third magnetic field sensor 56 (see FIG. 4) adapted to measure intensity of magnetic field 30 proximate surgical instrument 12. Third sensor 56 may be aligned such that its sense windings are substantially parallel to instrument axis 54. Thus, the distance from a reference point on surgical instrument 12 to target 14 may be calibrated as a function of the intensity of magnetic field 30.

Figure 5:
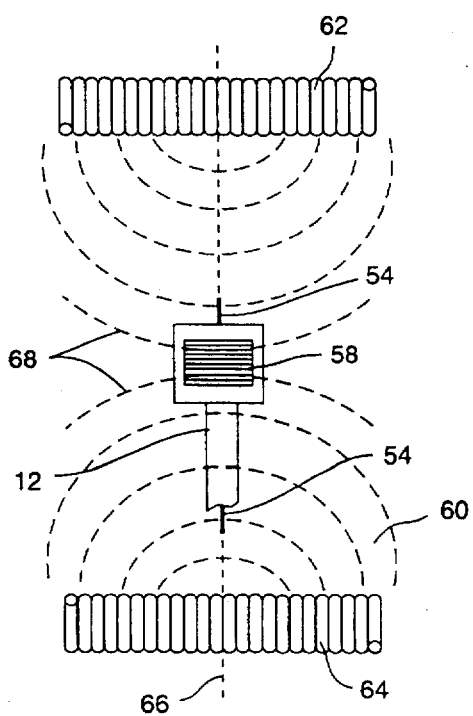
FIG. 5 shows the location of a magnetic field sensor relative to a surgical instrument within magnetic fields generated by two electromagnets.

Rather than utilizing two sensors at surgical instrument 12, system 10 may alternatively utilize a single magnetic field sensor 58, as shown in FIG. 5. FIG. 5 shows the location of sensor 58 relative to surgical instrument 12 within a magnetic field 60. In this alternate embodiment, each coordinate direction is associated with an upper electromagnet 62 and a lower electromagnet 64. Upper and lower electromagnets 62 and 64 are transversely aligned such that a center line 66 intersects upper and lower electromagnets 62 and 64 through their respective magnetic centers.

During surgery, upper electromagnet 62 is positioned above surgical probe 12 and lower electromagnet 64 is positioned below surgical instrument 12. As depicted in FIG. 5, sensor 58 detects zero magnitude in magnetic field 60 where magnetic flux lines 68 (alternatively generated by upper and lower electromagnets 62 and 64) are at substantially right angles to instrument axis 54. Although not shown in FIG. 5, this alternate embodiment employs a cooperating pair of electromagnets positioned perpendicularly to upper and lower electromagnets 62 and 64 (analogous to the perpendicular arrangement of first and second electromagnets 32 and 34 shown in FIGS. 2-3).

Figure 6:
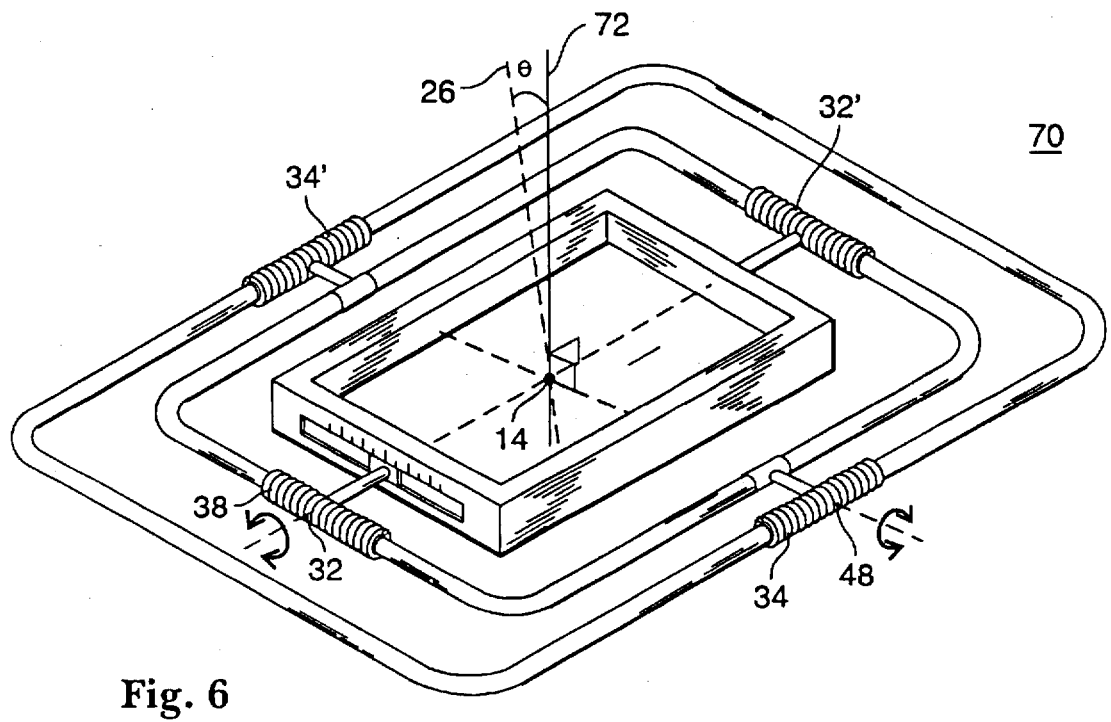
FIG. 6 is a perspective view of an exemplary magnetic field generator support frame.

With reference to FIG. 6, an exemplary support frame 70 for first and second electromagnets 32 and 34 is illustrated.

Body 16 is substantially immobilized with respect to support frame 70. Preferably, support frame 70 also supports body 16. Support frame 70 is preferably adjustable such that trajectory 26 intersects target 14 when magnetic field 30 is generated (see FIG. 3). For example, first electromagnet 32 may be translationally adjustable in a first coordinate direction and second electromagnet 34 may be translationally adjustable in a second coordinate direction.

Prior to surgery, support frame 70 is preferably adjusted such that magnetic centers 38 and 48 associated with first and second electromagnets 32 and 34 are aligned with target 14. The known location of target 14 may be translated into a coordinate system associated with the translational location of first and second magnetic centers 38 and 48. As such, the alignment between target 14 and first and second magnetic centers 38 and 48 may be verified by the surgeon.

Support frame 70 may also be adjustable to enable the surgeon to approach target 14 at a predetermined approach angle. Those skilled in the art will appreciate that the angle of trajectory 26 relative to a reference line may be altered by adjusting the angular position of first electromagnet 32 and/or second electromagnet 34. FIG. 6 depicts a vertical reference line 72, trajectory 26, and an approach angle relative to reference line 72. In this embodiment, support frame 70 incorporates a gimbal mechanism that allows first and second electromagnets 32 and 34 to rotate independently of one another. The translational and angular adjustability of support frame 70 gives the surgeon flexibility in planning trajectory 26. The gimbal mechanism of support frame 70 is shown for illustrative purposes and support frame 70 may be sized and shaped according to individual applications.

To ensure that system 10 properly detects the orientation of magnetic field 30, a third electromagnet 32' and a fourth electromagnet 34' may be employed. Third electromagnet 32' is configured such that its magnetic center (not shown) is aligned with magnetic center 38 of first electromagnet 32. In other words, the magnetic centers of electromagnets 32 and 32' both fall on first plane 44 (see FIG. 3). In addition, support frame 70 preferably incorporates a gimbal structure such that first and third electromagnets 32 and 32' cooperate when translationally or rotationally adjusted. Second and fourth electromagnets 34 and 34' are similarly arranged upon support frame 70. The cooperating electromagnet pairs ensures that the magnitude of magnetic field 30 is substantially symmetrical about target 14, which allows effective detection of misalignment of surgical instrument 12.

Support frame 70 is desirably configured such that first and third electromagnets 32 and 32' rotate about an axis defined by a line that intersects their respective magnetic centers. Similarly, second and fourth electromagnets 34 and 34' preferably rotate about an axis defined by a line that intersects their respective magnetic centers. In addition, target 14 is preferably located at the same height as first and second magnetic centers 38 and 48 by using conventional body immobilization techniques to fix body 16 relative to support frame 70. This configuration ensures that rotational adjustment of the electromagnets does not cause translational misalignment between trajectory 26 and target 14.

Figure 7:
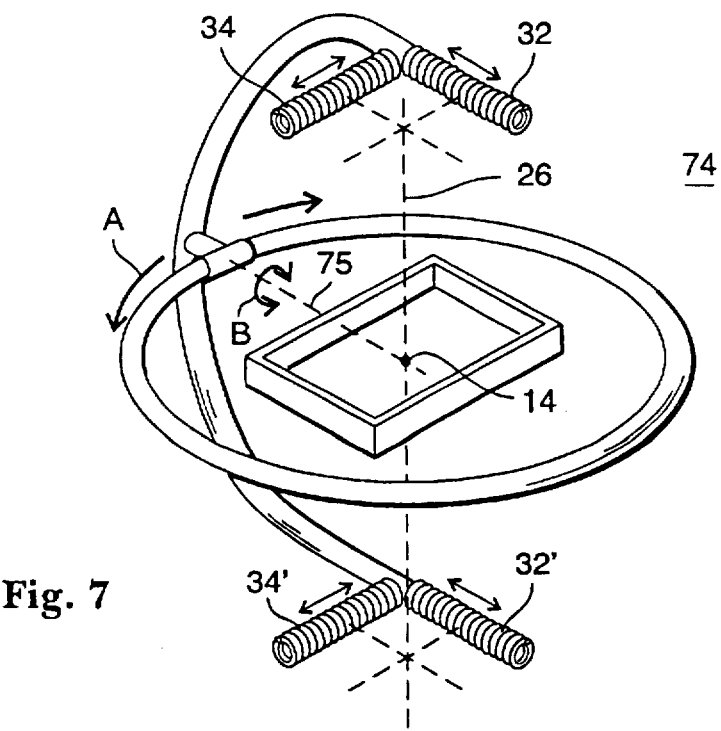
FIG. 7 is a perspective view of an alternate embodiment of the support frame.

FIG. 7 depicts an alternate embodiment in which a support frame 74 is adapted to support at least first and second electromagnets 32 and 34. Third and fourth electromagnets 32' and 34' may be positioned below first and second electromagnets 32 and 34 such that trajectory 26 intersects target 14 regardless of the approach angle. First and second electromagnets 32 and 34 are preferably in a fixed position relative to third and fourth electromagnets 32' and 34'.

Alternate support frame 74 preferably rotates on at least two independent axes of rotation to allow the surgeon to adjust the approach angle of trajectory 26. For example, alternate support frame 74 may be pivotable about a vertical axis to allow rotational adjustment in a horizontal plane (indicated as direction A). In addition, alternate support frame 74 may be pivotable about a horizontal axis 75 to allow rotational adjustment in the direction identified as direction B. Target 14 is desirably positioned such that it resides substantially on horizontal axis 75. As described above, the various electromagnets may be translationally adjustable along their corresponding longitudinal axes to facilitate alignment of trajectory 26 and target In an alternate embodiment, system 10 can be configured such that magnetic field generator 28 is a single electromagnet (not shown) mounted to surgical instrument 12. In addition, the magnetic field sensors are mounted to a support frame (not shown). In this alternate embodiment, the location of magnetic field 30 generated by magnetic field generator 28 varies according to the location of surgical instrument 12. At least two sensors are located upon the support frame such that trajectory 26 is indicated when the sensors simultaneously detect a null in magnetic field 30. As described above, magnetic field 30 includes geometric characteristics that are detectable by the sensors during operation of system 10. Before surgery, the surgeon can adjust the configuration of the support frame and/or the location of the sensors around the support frame to establish the position of trajectory 26 relative to the patient and the approach angle of trajectory 26 relative to target 14.

Figure 8:
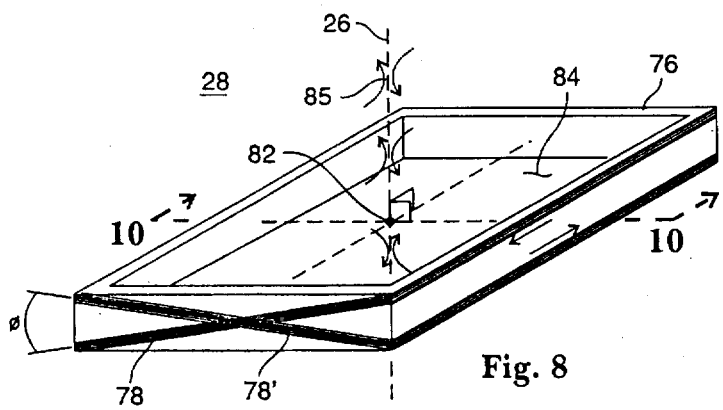
FIGS. 8 and 9 are perspective views of an alternate embodiment of a magnetic field generator.
Figure 9:
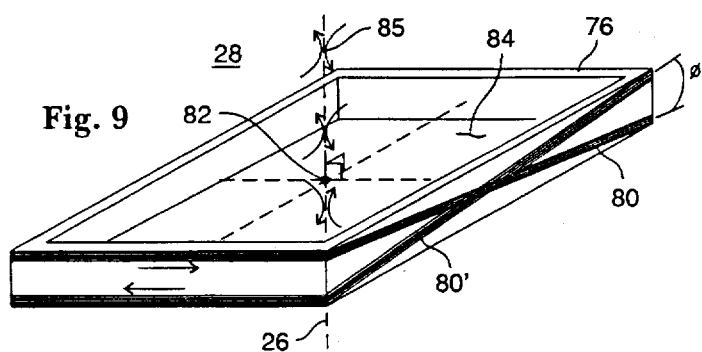

Referring to FIGS. 8–9, an alternate embodiment of magnetic field generator 28 is illustrated. In this embodiment, a frame 76 includes a number of magnetic wrappings situated around its external perimeter. A first wrapping 78 is situated such that it defines a plane that diagonally intersects frame 76. Similarly, a second wrapping 78' defines a plane that diagonally intersects frame 76 such that second wrapping 78' crosses first wrapping 78 at opposite sides of frame 76. First and second wrappings 78 and 78' are preferably associated with a first coordinate direction.

Frame 76 preferably includes a third wrapping 80 and a fourth wrapping 80' associated with a second coordinate direction. For clarity, FIG. 9 shows third and fourth wrappings 80 and 80' independently of first and second wrappings 78 and 78' However, first and second wrappings 78 and 78' are desirably combined with third and fourth wrappings 80 and 80' on frame 76. Third and fourth wrappings 80 and 80' cross each other on the sides of frame 76 where first and second wrappings 78 and 78' are parallel to each other. An angle $\phi$ between first and second wrappings 78 and 78' (and between third and fourth wrappings 80 and 80') may be selected according to the desired detection sensitivity of system 10. For satisfactory performance, angle $\phi$ is preferably twenty degrees or less.

Current flowing through the wrappings produces a magnetic field (not shown) that indicates trajectory 26. Trajectory 26 intersects a center 82 of frame 76 at substantially a right angle relative to a transverse plane 84 defined by frame 76. According to one aspect of this embodiment of magnetic field generator 28, current flows through first and second wrappings 78 and 78' in opposite directions (indicated by the arrows in FIG. 8). Similarly, current flows through third and fourth wrappings 80 and 80' in opposite directions.

First and second wrappings 78 and 78' and third and fourth wrappings 80 and 80' are alternately driven as cooperating wrapping pairs. As described above, the oscillation between the two wrapping pairs occurs at a preferred frequency of approximately 15–25 Hz. Due to the geometry of frame 76, the alignment of the wrapping pairs, and the current flow through the wrappings, the components 85 of the magnetic field along trajectory 26 are approximately equal in magnitude and opposite in direction. As described above, at least one sensor may be utilized to detect a null in the magnetic field when surgical instrument 12 is aligned with trajectory 26.

Figure 10:
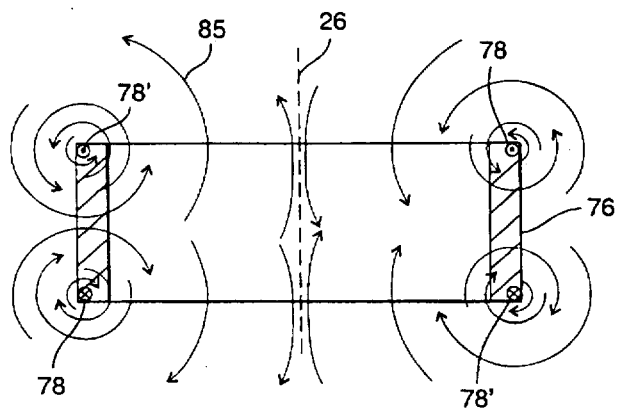
FIG. 10 cross sectional view of the magnetic field generator as viewed along the line 10—10 in FIG. 8.

With reference to FIG. 10, the orientation of magnetic field components 85 proximate trajectory 26 is illustrated in detail. FIG. 10 depicts a cross sectional view of magnetic field generator 28 as viewed along line 10—10 in FIG. 8. The current flow directions through first and second wrappings 78 and 78' are represented by points and crosses. The points represent current flow in a direction out of the page and the crosses represent current flow in a direction into the page. According to electromagnetic conventions, the directions of magnetic field components 85 follow the "right hand rule" as indicated in FIG. 10. Current flowing in the direction out of the page generates a counterclockwise magnetic field while current flowing in the direction into the page generates a clockwise magnetic field. Those skilled in the art will appreciate that magnetic field components 85 are substantially equal in magnitude and opposite in direction proximate trajectory 26.

Frame 76 may be translationally adjustable in a plurality of directions to enable the surgeon to align center 82 with target 14. In addition, frame 76 may be angularly adjustable about a plurality of axes to enable the surgeon to choose a desirable approach angle for trajectory 26. Of course, frame 76 need not be configured as shown in FIGS. 8–9, and those skilled in the art may adapt frame 76 as necessary for specific applications.

Figure 11:
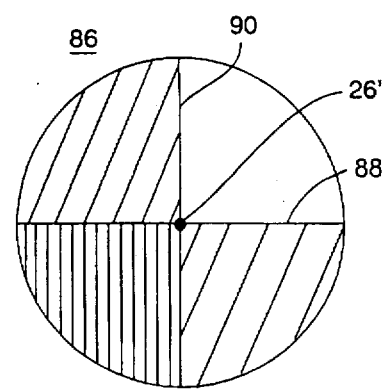
FIG. 11 shows a schematic view of a graphic guidance object utilized by the guidance system.

As described above, feedback device 24 indicates a position of surgical instrument 12 relative to trajectory 26. System 10 may employ conventional techniques for displaying graphic objects on a computer display terminal or other display device. Referring to FIG. 11, feedback device 24 is preferably configured to include a graphic guidance object 86. Other visual information may be provided to the surgeon along with graphic guidance object 86, such as tomogram images or live endoscopic video images (not shown).

According to the preferred embodiment, graphic guidance object 86 changes in real time to track movement of surgical instrument 12 proximate trajectory 26. Graphic guidance object 86 includes several features that indicate whether surgical instrument 12 currently resides on trajectory 26. If surgical instrument 12 does not reside on trajectory 26, then the relative orientation and positioning of these features indicate a direction in which to move surgical instrument 12 to cause surgical instrument 12 to align with trajectory 26. Alphanumeric position data or graphic objects (not shown) may inform the user of the distance between a reference point on surgical instrument 12 and target 14 at any given instant.

In the preferred embodiment, graphic guidance object 86 includes a horizontal pitch line 88 and a vertical yaw line 90, which together partition two-dimensional space into four quadrants. A trajectory point 26' resides at the intersection between pitch and yaw lines 88 and 90. Trajectory point 26' is a schematic representation of trajectory 26 as viewed looking toward target 14. In FIG. 11, pitch and yaw lines 88 and 90 represent cross sectional views of first and second planes 44 and 46 (see FIG. 3).

It should be appreciated that pitch and yaw lines 88 and 90 need not actually be drawn. Rather, the four quadrants may be defined to have contrasting colors. A light color may be utilized for the upper-right quadrant, medium colors may be utilized for the lower-right and upper-left quadrants, and a dark color may be utilized for the lower-left quadrant. Consequently, pitch and yaw lines 88 and 90 and trajectory point 26' may be easily implied by the intersections between quadrants of contrasting colors.

When instrument axis 54 is aligned with trajectory 26, pitch and yaw lines 88 and 90 intersect at substantially the center of graphic guidance object 86, as shown in FIG. 11. However, when instrument axis 54 is misaligned with trajectory 26, pitch and yaw lines 88 and 90 become off-centered. System 10 may detect misalignment of instrument axis 54 by sensing directional variations in magnetic field 30 or by sensing variations in the magnetic field intensity. Thus, a surgeon is able to guide surgical instrument 12 along trajectory 26 with the aid of graphic guidance object 86. System 10 tracks the alignment of surgical instrument 12 relative to trajectory 26 rather than locating the exact position of surgical instrument 12 at all times.

Figure 12:
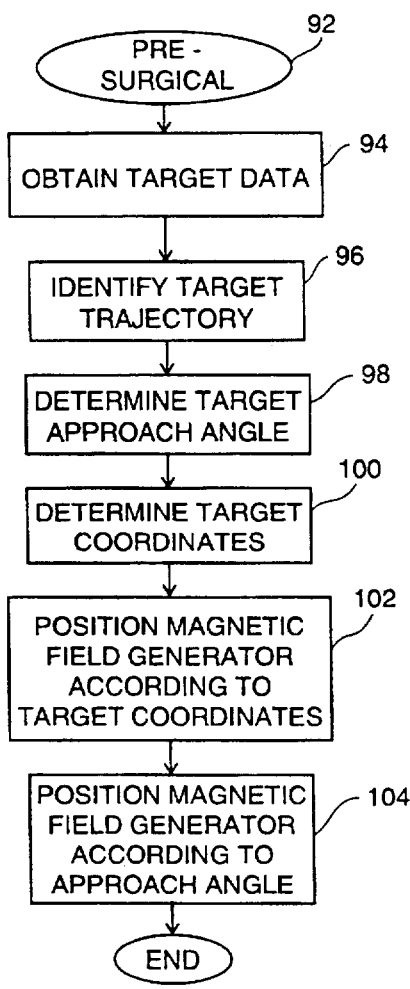
FIG. 12 is a flow diagram of a pre-surgical process.

Referring to FIG. 12, a pre-surgical process 92 is depicted as a flow diagram. Process 92 is performed to prepare system 10 for surgery, and one or more tasks of process 92 may be performed with human intervention. For convenience, process 92 is discussed in conjunction with the embodiment described above in connection with FIG. 6. It should be apparent to those skilled in the art that process 92 may also be performed for variations of system 10.

Pre-surgical process 92 begins with a task 94, which obtains data associated with target 14. Such data may include the position of target 14 relative to a stereotactic reference marker or the coordinate location of target 14 relative to a coordinate system. Typically, target data is obtained from CT scans, MRI scans, PET scans, or other images of body 16. Following task 94, a task 96 identifies trajectory 26 from an initial point 13 to target 14. The surgeon may rely upon his or her knowledge and experience to identify the most desirable trajectory 26 for the particular surgical procedure.

Next, a task 98 determines the target approach angle for trajectory 26. The location of target 14, the path of trajectory 26, and the position that body 16 will assume during surgery may affect the approach angle. For calibration purposes, the approach angle may be measured relative to reference line 72 (see FIG. 6) or any other suitable reference line through target 14. In addition to task 98, a task 100 determines the coordinates of target 14 relative to a coordinate system. Task 100, which may be performed by the surgeon, analyzes the location of target 14 relative to one or more imaging reference points to obtain the system coordinates of target 14.

After the coordinates of target 14 and the approach angle of trajectory 26 are determined, a task 102 is performed. Task 102 positions magnetic field generator 28 according to the target coordinates. The coordinate system is preferably associated with support frame 70, and first and second electromagnets 32 and 34 may be translationally adjusted such that trajectory 26 intersects target 14. Following task 102, a task 104 positions magnetic field generator 28 according to the approach angle determined in task 98. As described above, first and second electromagnets 32 and 34 may be independently rotated during task 104. Support frame 70 or electromagnets 32, 32', 34, or 34' may have printed scales or other markings to assist in the positioning during tasks 102 and 104. Following task 104, pre-surgical process 92 ends. In the alternate embodiment discussed above, tasks 102 and 104 may be performed to position the magnetic field sensors around support frame 70 rather than to position magnetic field generator 28 (which is located upon surgical instrument 12).

Figure 13:
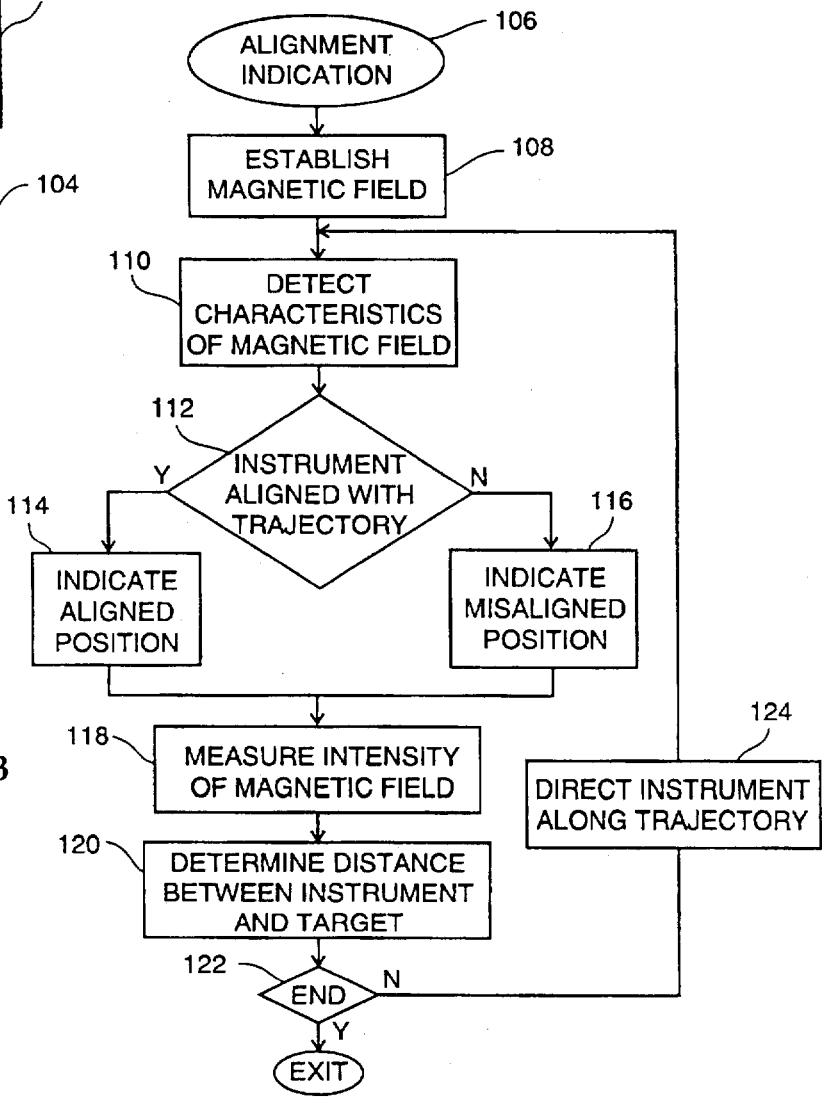
FIG. 13 is a flow diagram of an alignment indication process performed by the guidance system.

After pre-surgical process 92 is performed, system 10 may be utilized to assist the surgeon during the surgical procedure. With reference to FIG. 13, an alignment indication process 106 is illustrated as a flow diagram. Process 106 is performed by system 10 during the surgical procedure. As with process 92, process 106 is described with reference to the embodiment shown in FIG. 6. However, process 106 may be performed for any embodiment of the present invention.

Alignment indication process 106 begins with a task 108, which establishes magnetic field 30 proximate target 14. The geometric characteristics of magnetic field 30 are described above. As a result of process 92, first and second electromagnets 32 and 34 generate magnetic field 30 such that trajectory 26 is positioned as desired by the surgeon. Next, a task 110 detects the characteristics of magnetic field 30. First and second sensors 50 and 52 are preferably configured to detect the magnitude of magnetic field 30 in the direction of instrument axis 54. As described above in connection with FIG. 4, task 110 is preferably performed for the current location of surgical instrument 12. Following task 110, a query task 112 is prompted.

Query task 112 determines whether surgical instrument 12 is aligned with trajectory 26. As described above, if first and second sensors 50 and 52 simultaneously detect a null in magnetic field 30, then surgical instrument 12 is approximately aligned with trajectory 26. If query task 112 determines that surgical instrument 12 is aligned with trajectory 26, then a task 114 indicates that surgical instrument 12 is in an aligned position. In the preferred embodiment, task 114 causes graphic guidance object 86 to display a substantially central intersection of pitch and yaw lines 88 and 90 (see FIG. 11).

If query task 112 determines that surgical instrument 12 is misaligned with trajectory 26, then a task 116 is performed. Task 116 indicates a misaligned position of surgical instrument 12 by causing graphic guidance object 86 to display an off-centered intersection of pitch and yaw lines 88 and 90. As discussed above, misalignment of surgical instrument 12 may cause system 10 to detect variations in magnetic field strength or changes in the directional components of magnetic field 30. Thus, the surgeon can visually determine whether he or she is properly guiding the surgical instrument along trajectory 26. In addition, he or she can usually determine how to maneuver surgical instrument 12 into alignment with trajectory 26.

After either task 114 or task 116, a task 118 is performed. Task 118 measures the intensity of magnetic field 30 proximate surgical instrument 12. As described above, third sensor 56 may be configured to measure the intensity of magnetic field 30 in the direction parallel to instrument axis 54 (see FIG. 4). The magnetic field intensity measured in task 118 varies as a function of the distance between third sensor 56 and magnetic field generator 28. Thus, a task 120 utilizes the magnetic field intensity to determine the distance between surgical instrument 12 and target 14. The distance determined in task 120 is preferably displayed to the surgeon in an alphanumeric or graphic form (not shown).

Following task 120, a query task 122 is performed. Query task 122 determines whether to exit alignment indication process 106. For example, a user input from user interface 22 (see FIG. 1) may cause query task 122 to exit process 106.

Alternatively, query task 122 may exit process 106 when surgical instrument 12 reaches target 14. During process 106, system 10 may provide the surgeon with an endoscope view of target 14 along with other information related to the surgical procedure. When process 106 exits, system 10 may, for example, enlarge the endoscope view or highlight other display features that may require the surgeon's attention.

If query task 122 determines that alignment indication process 106 is not to be exited, then a task 124 is initiated. Task 124 directs surgical instrument 12 along trajectory 26. Task 124 is preferably performed by the surgeon with the aid of graphic guidance object 86. Following task 124, task 110 is reentered. As a result of continuously repeating this processing loop, process 106 causes system 10 to track movement of surgical instrument 12 in real time. Those skilled in the art will appreciate that the tasks described above in connection with process 106 require only relatively simple two-dimensional graphic techniques. Consequently, calculations may be performed quickly by conventional personal computers such that no perceivable lag results between movement of surgical instrument 12 and the resulting depiction of graphic guidance object 86.

In summary, the present invention provides an improved surgical guidance method and system for approaching a target within a body. The guidance system allows a surgeon to axially rotate a surgical instrument as he or she directs the instrument along a trajectory toward the target. The guidance system employs conventional electromagnetic components and may be implemented at a relatively low cost. The guidance system tracks the surgical instrument as it travels along the trajectory without quantitatively identifying the precise position of the surgical instrument during the surgical procedure. In addition, the guidance system may be configured with disposable sensor components, which may reduce the cost associated with sterilization.

The above description is of preferred embodiments of the present invention, and the invention is not limited to the specific embodiments described and illustrated. For example, the magnetic field generators may be configured to produce magnetic fields having a variety of different geometric characteristics, and the present invention is not limited to any specific arrangement of components. Nothing prevents the magnetic field generator from being instrument-mounted to cooperate with relatively stationary magnetic field sensors. In addition, the various process tasks need not be performed in any specific order, and equivalent results may be achieved utilizing a variety of different processing methodologies. Furthermore, many variations and modifications will be evident to those skilled in this art, and such variations and modifications are intended to be included within the spirit and scope of the invention, as expressed in the following claims.

What is claimed is:

1. A surgical guidance method for approaching a target along a trajectory extending between an initial point and said target, said method comprising the steps of:

establishing a magnetic field having geometric characteristics relative to said target such that said magnetic field has a predetermined orientation along said trajectory;

detecting a magnitude of said magnetic field in said predetermined orientation; and indicating, in response to said detecting step, a position of a surgical instrument relative to said trajectory.

2. A method according to claim 1, wherein said predetermined orientation of said magnetic field exists throughout said trajectory.

3. A method according to claim 1, wherein said predetermined orientation of said magnetic field is substantially constant throughout said trajectory.

4. A method according to claim 1, wherein:
said magnetic field has a magnetic center; and
said magnetic center is aligned with said target to form said trajectory.

5. A method according to claim 1, wherein said detecting step is performed by at least one magnetic sensor located at said surgical instrument.

6. A method according to claim 1, further comprising the step of determining a distance between said surgical instrument and said target, said determining step being responsive to said magnetic field.

7. A method according to claim 6, wherein said determining step measures an intensity of said magnetic field proximate said surgical instrument.

8. A method according to claim 1, wherein said magnetic field is comprised of a plurality of field components oriented such that said magnetic field has a substantially zero magnitude in a predetermined direction along said trajectory.

9. A surgical guidance method for approaching a target along a trajectory extending between an initial point and said target, said method comprising the steps of:
establishing a magnetic field having geometric characteristics relative to said target such that said magnetic field has a predetermined orientation along said trajectory, and said magnetic field having a magnetic center, said magnetic center being aligned with said target to form said trajectory;
detecting a magnitude of said magnetic field in said predetermined orientation, said detecting step comprising detecting said magnitude of said magnetic field at a first location and at a second location; and
indicating, in response to said detecting step, a position of a surgical instrument relative to said trajectory, said indicating step comprising indicating alignment of said surgical instrument and said trajectory when each of said first and second locations substantially intersects said trajectory.

10. A surgical guidance method for approaching a target along a trajectory extending between an initial point and said target, said method comprising the steps of:
establishing a magnetic field having geometric characteristics relative to said target such that said magnetic field has a predetermined orientation along said trajectory;
detecting a magnitude of said magnetic field in said predetermined orientation, said detecting step being performed by a pair of magnetic sensors spaced apart from one another and located at a surgical instrument, said surgical instrument having a longitudinal axis, and said magnetic sensors being located along said longitudinal axis; and
indicating, in response to said detecting step, a position of said surgical instrument relative to said trajectory.

11. A surgical guidance method for approaching a target along a trajectory extending between an initial point and said target, said method comprising the steps of:
establishing a magnetic field having geometric characteristics relative to said target such that said magnetic field has a predetermined orientation along said trajectory, said establishing step being performed by a magnetic field generator;
defining an imaginary reference line relative to said magnetic field generator;
determining an approach angle relative to said reference line;
positioning said magnetic field generator such that said trajectory substantially follows said approach angle;
detecting a magnitude of said magnetic field in said predetermined orientation; and
indicating, in response to said detecting step, a position of a surgical instrument relative to said trajectory.

12. A surgical guidance method for approaching a target along a trajectory extending between an initial point and said target, said method comprising the steps of:
determining, for said target, a set of target coordinates relative to a coordinate system; and
positioning a magnetic field generator relative to said set of target coordinates such that said trajectory intersects said target;
establishing a magnetic field having geometric characteristics relative to said target such that said magnetic field has a predetermined orientation along said trajectory, said establishing step being performed by said magnetic field generator;
detecting a magnitude of said magnetic field in said predetermined orientation; and
indicating, in response to said detecting step, a position of a surgical instrument relative to said trajectory.

13. A surgical guidance method for approaching a target within a body, said method comprising the steps of:
establishing a magnetic field proximate said target, said magnetic field having geometric characteristics, said geometric characteristics being configured to indicate a trajectory extending from an initial point to said target;
detecting said magnetic field proximate a surgical instrument; and
determining whether said surgical instrument is substantially aligned with said trajectory.

14. A method according to claim 13, further comprising the step of indicating, in response to said detecting step, a position of said surgical instrument relative to said trajectory.

15. A method according to claim 13, further comprising the step of determining a distance between said surgical instrument and said target, said determining step being responsive to said detecting step.

16. A method according to claim 13, wherein said magnetic field is comprised of a plurality of field components oriented such that said magnetic field has a substantially canceled magnitude in a predetermined direction along said trajectory.

17. A surgical guidance method for approaching a target within a body, said method comprising the steps of:
establishing a magnetic field proximate said target, said magnetic field having geometric characteristics, said geometric characteristics being configured to indicate a trajectory extending from an initial point to said target, and said establishing step being performed by a magnetic field generator;
defining an imaginary reference line relative to said magnetic field generator;
determining an approach angle relative to said reference line;
positioning said magnetic field generator such that said trajectory substantially follows said approach angle;
detecting said magnetic field proximate a surgical instrument; and determining whether said surgical instrument is substantially aligned with said trajectory.

18. A surgical guidance method for approaching a target within a body, said method comprising the steps of:

establishing a magnetic field proximate said target, said magnetic field having geometric characteristics, said geometric characteristics being configured to indicate a trajectory extending from an initial point to said target, said establishing step being performed by a magnetic field generator;

determining, for said target, a set of target coordinates relative to a coordinate system;

positioning said magnetic field generator relative to said set of target coordinates such that said trajectory intersects said target;

detecting said magnetic field proximate a surgical instrument; and determining whether said surgical instrument is substantially aligned with said trajectory.

19. A surgical guidance system for guiding a surgical instrument to a target within a body, said system comprising:

a magnetic field generator configured to produce a magnetic field having a geometric orientation along a trajectory extending from an initial point to said target;

means for detecting a difference from said geometric orientation in a location proximate said trajectory; and a feedback device in communication with said means for detecting, said feedback device being configured to indicate a position of said surgical instrument relative to said trajectory.

20. A surgical guidance system according to claim 19, further comprising means for supporting said magnetic field generator, said means for supporting being adjustable such that said trajectory intersects said target.

21. A surgical guidance system according to claim 20, wherein:

said magnetic field generator comprises a first generator element and a second generator element;

said first generator element is adjustable relative to a first coordinate direction; and said second generator element is adjustable relative to a second coordinate direction.

22. A method according to claim 19, wherein:

said magnetic field generator comprises a first electromagnet having a first magnetic center and a second electromagnet having a second magnetic center;

a first plane, substantially perpendicular to said first electromagnet, intersects said first magnetic center;

a second plane, substantially perpendicular to said second electromagnet, intersects said second magnetic center; and said first and second planes intersect at said trajectory.

23. A surgical guidance system according to claim 19, wherein said magnetic field sensor is adapted to removably couple with said surgical instrument.

24. A surgical guidance system according to claim 19, wherein said magnetic field generator comprises:

a support frame having a center and an external perimeter; and a plurality of magnetic wrappings situated around said external perimeter; wherein each of said magnetic wrappings is configured such that said trajectory intersects said center at substantially a right angle relative to a transverse plane defined by said support frame.

25. A surgical guidance system for guiding a surgical instrument to a target within a body, said system comprising:

a magnetic field generator configured to produce a magnetic field having a geometric orientation along a trajectory extending from an initial point to said target;

means for supporting said magnetic field generator, said means for supporting being adjustable such that said trajectory approaches said target at a predetermined approach angle relative to a reference line, said reference line being defined relative to said supporting means;

means for detecting a difference from said geometric orientation in a location proximate said trajectory; and a feedback device in communication with said means for detecting, said feedback device being configured to indicate a position of said surgical instrument relative to said trajectory.

* * * * *